(12) United States Patent
Sukumar et al.

(10) Patent No.: US 9,062,308 B2
(45) Date of Patent: Jun. 23, 2015

(54) COMPOSITIONS AND METHODS FOR TREATMENT OF TAMOXIFEN RESISTANT BREAST CANCER

(75) Inventors: Saraswati Sukumar, Columbia, MD (US); Kideok Jin, Parkville, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 14/002,183

(22) PCT Filed: Mar. 1, 2012

(86) PCT No.: PCT/US2012/027185
§ 371 (c)(1),
(2), (4) Date: Oct. 8, 2013

(87) PCT Pub. No.: WO2012/118915
PCT Pub. Date: Sep. 7, 2012

(65) Prior Publication Data
US 2014/0171483 A1 Jun. 19, 2014

Related U.S. Application Data

(60) Provisional application No. 61/448,009, filed on Mar. 1, 2011.

(51) Int. Cl.
*C12Q 1/68* (2006.01)
*C07H 21/02* (2006.01)
*C07H 21/04* (2006.01)
*C12N 15/113* (2010.01)
*A61K 31/713* (2006.01)

(52) U.S. Cl.
CPC ............ *C12N 15/113* (2013.01); *A61K 31/713* (2013.01); *C12N 15/1135* (2013.01); *C12N 2310/14* (2013.01); *C12N 2310/141* (2013.01); *C12Q 1/6886* (2013.01); *C12Q 1/6897* (2013.01)

(58) Field of Classification Search
USPC .................................. 435/6.1, 91.1, 325, 375
See application file for complete search history.

(56) References Cited

U.S. PATENT DOCUMENTS

2010/0285031 A1  11/2010  Sukumar et al.

FOREIGN PATENT DOCUMENTS

| WO | 03012052 A2 | 2/2003 |
| WO | 2008115419 A2 | 9/2008 |
| WO | 2008115470 A2 | 9/2009 |

OTHER PUBLICATIONS

Braig, S., et al., "MicroRNA miR-196a is a central regulator of HOX-B7 and BMP expression in malignant melanoma", Cellular and Molecular Life Sciences, vol. 67, No. 20, pp. 3535-3548, May 18, 2010.

(Continued)

*Primary Examiner* — Terra Cotta Gibbs
(74) *Attorney, Agent, or Firm* — Johns Hopkins Technology Transfer

(57) ABSTRACT

The inventors found that the gene, HOXB7, was frequently overexpressed in breast cancer, and is a major upstream regulator of events leading to tamoxifen resistance. The present invention provides double-stranded short interfering nucleic acid (siNA) molecules that targets the HOXB7 gene in cells, and also provides methods of use of this siNA molecule for methods of screening, diagnosis and prediction of treatment outcomes as well as treatment of cancer.

2 Claims, 12 Drawing Sheets

(56) References Cited

OTHER PUBLICATIONS

Jin, K., et al., "The HOXB7 protein renders breast cancer cells resistant to tamoxifen through activation of the EGFR pathway", Proceedings of the National Academy of Sciences, vol. 109, No. 8, pp. 2736-2741, Jun. 20, 2011.

Nishi, H., et al., "Early growth response-1 Gene mediates up-regulation of epidermal growth factor receptor expression during hypoxia", Cancer research, Feb. 1, 2002, vol. 62, No. 3, pp. 827-834.

Ma, X., et al., "A two-gene expression ratio predicts clinical outcome in breast cancer patients treated with tamoxifen", Cancer Cell, Jun. 2004, vol. 5, No. 6, pp. 607-616.

SEQUENCE LISTING

```
<160> NUMBER OF SEQ ID NOS: 7

<210> SEQ ID NO 1
<211> LENGTH: 19
<212> TYPE: DNA
<213> ORGANISM: Artificial
<220> FEATURE:
<223> OTHER INFORMATION: siNA sequence

<400> SEQUENCE: 1
atatccagcc tcaagttcg                                            19

<210> SEQ ID NO 2
<211> LENGTH: 19
<212> TYPE: DNA
<213> ORGANISM: Artificial
<220> FEATURE:
<223> OTHER INFORMATION: siNA sequence

<400> SEQUENCE: 2
acttcttgtg cgtttgctt                                            19

<210> SEQ ID NO 3
<211> LENGTH: 17
<212> TYPE: DNA
<213> ORGANISM: Artificial
<220> FEATURE:
<223> OTHER INFORMATION: Forward primer for EGFR promoter region

<400> SEQUENCE: 3
caaggccagc ctctgat                                              17

<210> SEQ ID NO 4
<211> LENGTH: 20
<212> TYPE: DNA
<213> ORGANISM: Artificial
<220> FEATURE:
<223> OTHER INFORMATION: Reverse primer for EGFR promoter region

<400> SEQUENCE: 4
cccctttccc ttcttttgtt                                           20

<210> SEQ ID NO 5
<211> LENGTH: 22
<212> TYPE: DNA
<213> ORGANISM: Artificial
<220> FEATURE:
<223> OTHER INFORMATION: HOXB7 PCR forward primer

<400> SEQUENCE: 5
aaaacctacc actcgcgtgt tc                                        22
```

```
<210> SEQ ID NO 6
<211> LENGTH: 18
<212> TYPE: DNA
<213> ORGANISM: Artificial
<220> FEATURE:
<223> OTHER INFORMATION: HOXB7 PCR reverse primer

<400> SEQUENCE: 6
ggacgggaag caagaagc                                                  18

<210> SEQ ID NO 7
<211> LENGTH: 17
<212> TYPE: DNA
<213> ORGANISM: Artificial
<220> FEATURE:
<223> OTHER INFORMATION: fluorogenic MGB probe sequence n=inosine
<220> FEATURE:
<221> NAME/KEY: misc_feature
<222> LOCATION: (2)..(2)
<223> OTHER INFORMATION: n is a, c, g, or t

<400> SEQUENCE: 7
vnccaagcgc ctggctg                                                   17
```

COMPOSITIONS AND METHODS FOR TREATMENT OF TAMOXIFEN RESISTANT BREAST CANCER

REFERENCE TO RELATED APPLICATIONS

This application is a 35 U.S.C. § 371 U.S. National Stage entry of International Application PCT/US2012/027185, having an international filing date of Mar. 1, 2012, which claims the benefit of U.S. Provisional Application 61/448,009, filed Mar. 1, 2011, the contents of both of which are incorporated herein by reference in its entirety.

INCORPORATION-BY-REFERENCE OF MATERIAL SUBMITTED ELECTRONICALLY

The instant application contains a Sequence Listing which has been submitted in ASCII format via EFS-Web and is hereby incorporated by reference in its entirety. Said ASCII copy, created on Mar. 01, 2012, is named P11436-02_SEQ_ST25.txt and is 1,695 bytes in size.

STATEMENT OF GOVERNMENTAL INTEREST

This invention was made with U.S. government support under NIH grant no. P50-CA88843. The U.S. government has certain rights in the invention.

BACKGROUND OF THE INVENTION

In postmenopausal women with early-stage estrogen receptor-α (ERα)-positive breast cancer (ER+), the selective estrogen-receptor modulator (SERM), tamoxifen (TAM) represents a major adjuvant treatment in clinical practice. Many of the breast tumors that initially respond to the TAM therapy eventually develop resistance and recur. Among the patients with breast cancer with acquired resistance, only 20% of patients who progress on TAM respond to the selective ER down-regulator, fulvestrant, or to aromatase inhibitors even if ERα expression is maintained and regulates tumor proliferation.

Homeobox genes are regulatory genes encoding nuclear proteins that act as transcription factors during normal development and differentiation. One of these, HOXB7, is involved in a variety of developmental processes, including hematopoietic differentiation and lymphoid and mammary gland development. The role of HOX genes in breast cancer development is largely unexplored.

A need, therefore, still exists a need for improved treatment of TAM resistant breast cancer.

SUMMARY OF THE INVENTION

The embodiments of the present invention provide evidence that HOXB7 overexpression in ER+ breast cancer cells confers TAM resistance through increased expression and signaling of EGFR. The present invention teaches that elevation of HOXB7 expression is a key step in the acquisition and maintenance of SERM resistance in breast cancer.

The embodiments of the present invention provide evidence that HOXB7 overexpression in ER+ breast cancer cells confers TAM resistance through increased expression and signaling of HER2. The present invention teaches that elevation of HOXB7 expression is a key step in the acquisition and maintenance of SERM resistance in breast cancer.

In accordance with an embodiment, the present invention provides a double-stranded short interfering nucleic acid (siNA) molecule comprising a first strand and a second strand having complementarity to each other, wherein at least one strand comprises at least 15 nucleotides of SEQ ID NO: 1 and/or SEQ ID NO: 2.

In accordance with another embodiment, the present invention provides a double-stranded siNA molecule comprising a first strand and a second strand having complementarity to each other, wherein at least one strand comprises at least 15 nucleotides of SEQ ID NO: 1 and/or SEQ ID NO: 2, and wherein at least one nucleotide is a chemically modified nucleotide.

In accordance with still another embodiment, the present invention provides a pharmaceutical composition comprising the comprising a first strand and a second strand having complementarity to each other, wherein at least one strand comprises at least 15 nucleotides of SEQ ID NO: 1 and/or SEQ ID NO: 2, in a pharmaceutically acceptable carrier or diluent.

In accordance with a further embodiment, the present invention provides a pharmaceutical composition comprising the comprising a first strand and a second strand having complementarity to each other, wherein at least one strand comprises at least 15 nucleotides of SEQ ID NO: 1 and/or SEQ ID NO: 2, and wherein at least one nucleotide is a chemically modified nucleotide, in a pharmaceutically acceptable carrier or diluent.

In accordance with an embodiment, the present invention provides a vector comprising a double-stranded siNA molecule comprising a first strand and a second strand having complementarity to each other, wherein at least one strand comprises at least 15 nucleotides of SEQ ID NO: 1 and/or SEQ ID NO: 2.

In accordance with another embodiment, the present invention provides a vector comprising a double-stranded siNA molecule comprising a first strand and a second strand having complementarity to each other, wherein at least one strand comprises at least 15 nucleotides of SEQ ID NO: 1 and/or SEQ ID NO: 2 and wherein at least one nucleotide is a chemically modified nucleotide.

In accordance with yet another embodiment, the present invention provides a method of modulating expression of a target gene in a host cell or population of cells comprising administering to the cell or population of cells a double-stranded siNA molecules described above, or the pharmaceutical composition described above, or the vector described above, in an amount sufficient to modulate target gene expression with the host cell or population of cells.

In accordance with still another embodiment, the present invention provides a method of modulating expression of a target gene in a host cell or population of cells comprising administering to the cell or population of cells the double-stranded siNA molecules described above, or the pharmaceutical composition described above, or the vector described above, in an amount sufficient to modulate target gene expression with the host cell or population of cells in an amount sufficient to modulate target gene expression with the host cell or population of cells and diagnose the role of the target gene in a clinical condition or disease.

In accordance with a further embodiment, the present invention provides the use of the double-stranded siNA molecules described above, or the pharmaceutical composition described above, or the vector described above, in an effective amount, to prepare a medicament, preferably for use as a medicament for treating a disease in a subject.

In accordance with a further embodiment, the present invention provides a method of treating a human subject suffering from a condition which is mediated by the action, or by loss of action, of HOXB7, which comprises administering to said subject an effective amount of the double-stranded siNA molecules described above, or the pharmaceutical composition described above, or the vector described above.

In accordance with an embodiment, the present invention provides a method of an increased risk of non-responsiveness to treatment with tamoxifen in a patient suffering from breast cancer comprising: a) obtaining a sample of genetic material from tumor of the patient, b) assaying the sample for the level of expression of HOXB7 in the tumor which is associated with an increased risk of non-responsiveness to treatment with tamoxifen, and c) predicting the an increased risk of non-responsiveness to treatment with tamoxifen in the patient based on the level of expression of HOXB7 in the tumor, wherein when the level of expression of HOXB7 is elevated when compared to a reference control level there is an increased risk of non-responsiveness of the tumor to tamoxifen.

In accordance with another embodiment HOXB7 overexpression can be the result of expression of mir196a. It was found that miR196a can control HOXB7 expression, and that reducing miR196a levels in tamoxifen-resistant cells causes an increase of HOXB7 expression. Further, miRNA 196a is regulated by c-MYC which undergoes stabilization through the EGFR-HER2 signaling pathway. Thus ways of increasing mir196a levels would result in decrease of HOXB7 expression and reversal of TAM resistance.

In accordance with another embodiment, the present invention provides a method predicting a clinical outcome after treatment with tamoxifen in a patient suffering from breast cancer comprising: a) obtaining a sample of genetic material from tumor of the patient, b) assaying the sample for the level of expression of HOXB7 in the tumor which is associated with the outcome of treatment with tamoxifen, and c) predicting the outcome of treatment with tamoxifen in the patient based on the level of expression of HOXB7 in the tumor, wherein when the level of expression of HOXB7 is elevated when compared to a reference control level there is a decrease in relapse-free survival outcome.

In accordance with another embodiment, the present invention provides a method for screening compounds useful for treatment of breast cancer comprising a) obtaining a candidate compound, b) contacting the candidate compound with a test cell which expresses HOXB7, for a sufficient period of time, c) measuring the amount of HOXB7 expression in the cell and comparing the amount of expression measured with a control cell, and d) determining whether the candidate compound suppressed expression of HOXB7 in the test cell.

DETAILED DESCRIPTION OF THE INVENTION

Figure 1A:
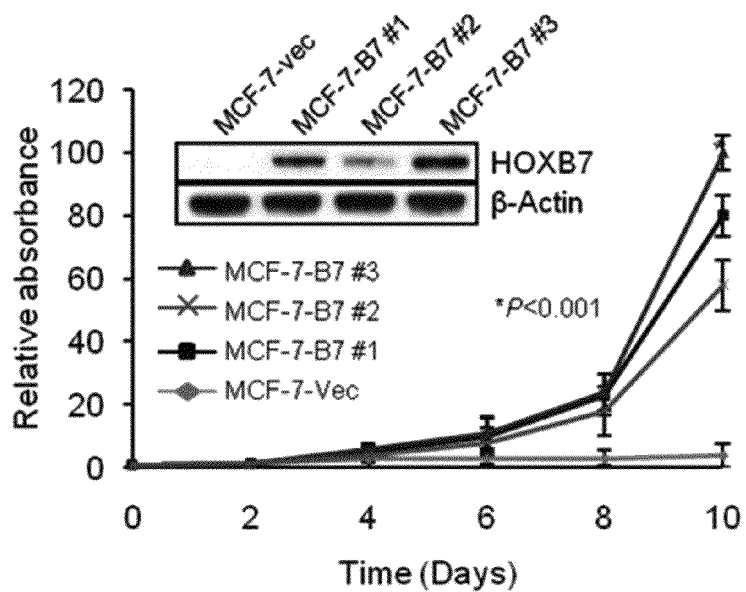
FIG. 1 depicts the effect of HOXB7 expression in breast cancer cells. (1A) Immunoblot analysis of HOXB7 expression in MCF-7-Vec and MCF-7-B7 cells (3 clones; MCF-7-B7 #1, #2 and #3) and growth curve of MCF-7-Vec and MCF-7-B7 cells grown in monolayer culture and (1B) soft agar colony formation by MCF-7-Vec and MCF-7-B7 cells. (1C) $T_1$-weighted $^1$H MR imaging of MCF-7-B7 cells, and MCF-7-vec cells visualizing the degradation of ECM over a period of time as indicated. (1D) Representative 3D reconstructed images of vascular volume maps (row 1), permeability-surface area product (row 2) and combined vascular volume and permeability-surface area product (row 3) for MCF-7 parental (column 1), MCF-7-Vec (column 2), and MCF-7-B7 (column 3) tumors in mice. (1E) Tumor growth curves of MCF-7-Vec and MCF-7-B7 cells implanted s.c. in athymic mice in presence of an exogenous slow release, estrogen implant and (1F) in absence of exogenous estrogen supplementation.

Molecular adaptations during acquired TAM-resistance utilize multiple signaling pathways which are well documented in the literature. The present invention shows that: 1) MCF-7 cells treated over extended periods with TAM in vitro develop TAM-resistance, which is accompanied, by a parallel, elevated expression of HOXB7 and EGFR, events that also occur in another two different commonly used anti-estrogen resistance models; 2) these molecular events are largely recapitulated in MCF-7 cells by overexpression of a single gene, HOXB7, leading to acquired resistance to TAM; 3) siRNA-mediated silencing of HOXB7 significantly reversed many of the malignant traits and molecular changes in both the native (BT474) and engineered anti-estrogen resistance models; and 4) preliminary evidence of potential clinical relevance was observed in a small discovery cohort of ER+ breast cancer patients who received TAM monotherapy, where a higher level of HOXB7 in the cancer specimens correlated significantly to a poor relapse-free survival. Thus, HOXB7 is a major upstream regulator of events leading to TAM-resistance in breast cancer.

In accordance with an embodiment, the present invention provides double-stranded siNA molecules comprising a first strand and a second strand having complementarity to each other, wherein at least one strand comprises at least 15 nucleotides of SEQ ID NO: 1 and/or SEQ ID NO: 2.

In accordance with another embodiment, the present invention provides a method of modulating expression of a target gene in a host cell or population of cells comprising administering to the cell or population of cells the double-stranded siNA molecules described above, or the pharmaceutical composition described above, or the vector described above, in an amount sufficient to modulate target gene expression with the host cell or population of cells in an amount sufficient to modulate target gene expression with the host cell or population of cells and diagnose the role of the target gene in a clinical condition or disease. In one or more embodiments, the target gene is HOXB7. In one or more other embodiments the disease is cancer, preferably breast cancer.

In accordance with a further embodiment, the present invention provides the use of the double-stranded siNA molecules described above, or the pharmaceutical composition described above, or the vector described above, in an effective amount, to prepare a medicament, preferably for use as a medicament for treating a disease in a subject. In one or more embodiments, the medicament further comprises a second therapeutic agent. The second therapeutic agent can be any known agent suitable for use in treating mammals or humans. It is contemplated that there can be more than two therapeutic agents as well.

In accordance with yet another embodiment, the above methods further comprise increasing the level of expression of miRNA-196a in a host cell or population of cells. The increased level of expression is understood to decrease HOXB7 expression, and thereby decrease TAM resistance. Methods of transfecting cells with miRNA are known in the art, including, for example, transfection with lentiviral vectors comprising the miRNA of interest. See, for example, Cancer Res., 70(14):5923-5930 (2010); and Mol. Therapy, 18(1):181-187 (2010).

In accordance with an embodiment, the second therapeutic agent can be an agent associated with treatment of cancer in a subject. Examples of such agents include, but are not limited to, paclitaxel, anastrozole, exemestane, fulvestrant, letrozole, gemcitabine, trastuzumab, pegfilgrastim, filgrastim, epotein, taxol, and others. In another embodiment, the second therapeutic agent is an agent that can increase the level of expression of miRNA-196a in a host cell or population of cells.

The term "polynucleotide," as used herein, includes and/or is synonymous with "nucleic acid," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide.

The term "polyribonucleotide," as used herein, includes "ribonucleic acid," "oligoribonucleotide," and "ribonucleic acid molecule," and generally means a polymer of RNA which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. It may be suitable in some instances, in an embodiment, for the nucleic acids to comprise one or more insertions, deletions, inversions, and/or substitutions.

Preferably, the nucleic acids of the invention are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

The nucleic acids can be constructed based on chemical synthesis and/or enzymatic ligation reactions using procedures known in the art. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Macromolecular Resources (Fort Collins, Colo.) and Synthegen (Houston, Tex.).

In another embodiment, the present invention provides one or more polyribonucleotide molecules which are selected from the group consisting of single stranded RNA, double stranded RNA, micro-RNA (miRNA), short-hairpin RNA (shRNA), and/or analogs thereof.

The present invention also relates to compounds, compositions, and methods useful for modulating the expression and activity of a target gene of interest, or expression and/or activity by RNAi using small nucleic acid molecules. As used herein, the instant invention features small nucleic acid molecules, or polyribonucleotides, and includes terms such as such as siRNA, siNA, dsRNA, miRNA, and shRNA molecules and methods used to modulate the expression of target genes of interest.

A polyribonucleotide of the invention can be unmodified or chemically modified. A polyribonucleotide of the instant invention can be chemically synthesized, expressed from a vector or enzymatically synthesized. The instant invention also features various chemically modified polyribonucleotides, including, for example, siRNA molecules capable of modulating repeat expansion gene expression or activity in cells by RNAi. The use of chemically modified siRNA improves various properties of native siRNA molecules through increased resistance to nuclease degradation in vivo and/or through improved cellular uptake.

In one embodiment, the polyribonucleotide molecule of the present invention comprises modified nucleotides while maintaining the ability to mediate RNAi. The modified nucleotides can be used to improve in vitro or in vivo characteristics, such as stability, activity, and/or bioavailability. For example, when the polyribonucleotide molecule is a siRNA molecule, the invention can comprise modified nucleotides as a percentage of the total number of nucleotides present in the siRNA molecule. As such, an siRNA molecule of the invention can generally comprise about 5% to about 100% modified nucleotides (e.g., 5%, 10%, 15%, 20%, 25%, 30%, 35%, 40%, 45%, 50%, 55%, 60%, 65%, 70%, 75%, 80%, 85%, 90%, 95% or 100% modified nucleotides). The actual percentage of modified nucleotides present in a given siRNA molecule will depend on the total number of nucleotides present in the siRNA. If the siRNA molecule is single-stranded, the percent modification can be based upon the total number of nucleotides present in the single-stranded siRNA molecules. Likewise, if the siRNA molecule is double-stranded, the percent modification can be based upon the total number of nucleotides present in the sense strand, antisense strand, or both the sense and antisense strands.

The term "modulate," as used herein means that the expression of the target gene, or level of RNA molecule or equivalent RNA molecules encoding one or more target proteins or protein subunits, or activity of one or more proteins or protein subunits is up regulated or down regulated, such that expression, level, or activity is greater than or less than that observed in the absence of the modulator. For example, the term "modulate" can mean "inhibit," but the use of the word "modulate" is not limited to this definition.

The terms "inhibit," "down-regulate," "reduce," or "knockdown," as used herein, means that the expression of the target gene, or level of RNA molecules or equivalent RNA molecules encoding one or more target proteins or protein subunits, or activity of one or more target proteins or protein subunits, is reduced below that observed in the absence of the polyribonucleotide molecules (e.g., siRNA) of the invention. In an embodiment, inhibition, down-regulation or reduction with a siRNA molecule is below that level observed in the presence of an inactive or attenuated molecule. In another embodiment, inhibition, down-regulation, or reduction with siRNA molecules is below that level observed in the presence of, for example, a siRNA molecule with scrambled sequence or with mismatches. In another embodiment, inhibition, down-regulation, or reduction of target gene expression with a nucleic acid molecule of the instant invention is greater in the presence of the nucleic acid molecule than in its absence.

In accordance with an embodiment of the present invention, the amount of time of exposure of the siNA compositions to the host cells, population of cells or subject should be sufficiently long to effect gene "knockdown" or modulation of the expression of the target gene in the host cell, population of cells or in the subject. The time for the desired effect varies with dosage, target, age and other factors known to those of skill in the art. Generally, the time of exposure of the siNA compositions to the host cells, population of cells or subject should range from about 1 hour to about 120 hours, preferably from about 1 hour to about 48 hours, more preferably from about 1 hour to about 24 hours.

By "gene", or "target gene", is meant, a nucleic acid that encodes a RNA, for example, nucleic acid sequences including, but not limited to, structural genes encoding a polypeptide. A gene or target gene can also encode a functional RNA (fRNA) or non-coding RNA (ncRNA), such as small temporal RNA (stRNA), miRNA, small nuclear RNA (snRNA), siRNA, small nucleolar RNA (snRNA), ribosomal RNA (rRNA), transfer RNA (tRNA) and precursor RNAs thereof. Such non-coding RNAs can serve as target nucleic acid molecules for siRNA mediated RNA interference in modulating the activity of fRNA or ncRNA involved in functional or regulatory cellular processes. Aberrant fRNA or ncRNA activity leading to disease can therefore be modulated by polyribonucleotide molecules of the invention. Polyribonucleotide molecules targeting fRNA and ncRNA can also be used to manipulate or alter the genotype or phenotype of an organism or cell, by intervening in cellular processes such as genetic imprinting, transcription, translation, or nucleic acid processing (e.g., transamination, methylation etc.). The target gene can be a gene derived from a cell, an endogenous gene, a transgene, or exogenous genes such as genes of a pathogen, for example a virus, which is present in the cell after infection thereof.

As used herein, the term "complementarity" or "complementary" means that a nucleic acid can form hydrogen bond(s) with another nucleic acid sequence by either traditional Watson-Crick or other non-traditional types. In reference to the polyribonucleotide molecules of the present invention, the binding free energy for a nucleic acid molecule with its complementary sequence is sufficient to allow the relevant function of the nucleic acid to proceed, e.g., RNAi activity. Determination of binding free energies for nucleic acid molecules is well known in the art (see, e.g., Turner et al., 1987, *CSH Symp. Quant. Biol.* LII pp. 123-133; Frier et al., 1986, *Proc. Nat. Acad. Sci. USA* 83:9373-9377; Turner et al., 1987, *J. Am. Chem. Soc.* 109:3783-3785). A percent complementarity indicates the percentage of contiguous residues in a nucleic acid molecule that can form hydrogen bonds (e.g., Watson-Crick base pairing) with a second nucleic acid sequence (e.g., 5, 6, 7, 8, 9, or 10 nucleotides out of a total of 10 nucleotides in the first oligonucleotide being based paired to a second nucleic acid sequence having 10 nucleotides represents 50%, 60%, 70%, 80%, 90%, and 100% complementary respectively).

As used herein, the term "RNA" means a molecule comprising at least one ribonucleotide residue. By "ribonucleotide" is meant a nucleotide with a hydroxyl group at the 2' position of a β-D-ribo-furanose moiety. The terms "RNA," "ribonucleotides" and "polyribonucleotide," also include double-stranded RNA, single-stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Such alterations can include addition of non-nucleotide material, such as to the end(s) of the siRNA, or internally, for example, at one or more nucleotides of the RNA. Nucleotides in the RNA molecules of the instant invention can also comprise non-standard nucleotides, such as non-naturally occurring nucleotides or chemically synthesized nucleotides or deoxynucleotides. These altered RNAs can be referred to as analogs or analogs of naturally-occurring RNA.

With respect to siNA compositions described herein, the carrier can be any of those conventionally used, and is limited only by physico-chemical considerations, such as solubility and lack of reactivity with the active compound(s), and by the route of administration. The carriers described herein, for example, vehicles, adjuvants, excipients, and diluents, are well-known to those skilled in the art and are readily available to the public. It is preferred that the carrier be one which is chemically inert to the active agent(s), and one which has little or no detrimental side effects or toxicity under the conditions of use. Examples of the carriers include soluble carriers such as known buffers which can be physiologically acceptable (e.g., phosphate buffer) as well as solid compositions such as solid-state carriers or latex beads.

The carriers or diluents used herein may be solid carriers or diluents for solid formulations, liquid carriers or diluents for liquid formulations, or mixtures thereof.

Solid carriers or diluents include, but are not limited to, gums, starches (e.g., corn starch, pregelatinized starch), sugars (e.g., lactose, mannitol, sucrose, dextrose), cellulosic materials (e.g., microcrystalline cellulose), acrylates (e.g., polymethylacrylate), calcium carbonate, magnesium oxide, talc, or mixtures thereof.

For liquid formulations, pharmaceutically acceptable carriers may be, for example, aqueous or non-aqueous solutions, or suspensions. Examples of non-aqueous solvents are propylene glycol, polyethylene glycol, and injectable organic esters such as ethyl oleate. Aqueous carriers include, for example, water, alcoholic/aqueous solutions, cyclodextrins, emulsions or suspensions, including saline and buffered media.

Parenteral vehicles (for subcutaneous, intravenous, intraarterial, or intramuscular injection) include, for example, sodium chloride solution, Ringer's dextrose, dextrose and sodium chloride, lactated Ringer's and fixed oils. Formulations suitable for parenteral administration include, for example, aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

Intravenous vehicles include, for example, fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions.

The choice of carrier will be determined, in part, by the particular siNA containing compositions, as well as by the particular method used to administer the composition. Accordingly, there are a variety of suitable formulations of the pharmaceutical compositions of the invention. The following formulations for parenteral, subcutaneous, intravenous, intramuscular, intraarterial, intrathecal and interperitoneal administration are exemplary, and are in no way limiting. More than one route can be used to administer the siNA compositions of the present invention, and in certain instances, a particular route can provide a more immediate and more effective response than another route.

Injectable formulations are in accordance with the invention. The requirements for effective pharmaceutical carriers for injectable compositions are well-known to those of ordinary skill in the art (see, e.g., *Pharmaceutics and Pharmacy Practice*, J.B. Lippincott Company, Philadelphia, Pa., Banker and Chalmers, eds., pages 238-250 (1982), and *ASHP Handbook on Injectable Drugs*, Trissel, 15th ed., pages 622-630 (2009)).

As used herein the term "pharmaceutically active compound" or "therapeutically active compound" means a compound useful for the treatment or modulation of a disease or condition in a subject suffering therefrom. Examples of pharmaceutically active compounds can include any drugs known in the art for treatment of disease indications. A particular example of a pharmaceutically active compound is a chemotherapeutic agent.

The term "chemotherapeutic agent" as well as words stemming therefrom, as used herein, generally includes pharmaceutically or therapeutically active compounds that work by interfering with DNA synthesis or function in cancer cells. Based on their chemical action at a cellular level, chemotherapeutic agents can be classified as cell-cycle specific agents (effective during certain phases of cell cycle) and cell-cycle nonspecific agents (effective during all phases of cell cycle). Without being limited to any particular example, examples of chemotherapeutic agents can include alkylating agents, angiogenesis inhibitors, aromatase inhibitors, antimetabolites, anthracyclines, antitumor antibiotics, monoclonal antibodies, platinums, topoisomerase inhibitors, and plant alkaloids.

In accordance with an embodiment, the present invention can include a composition wherein the chemotherapeutic agent is a second therapeutic agent included in the composition of the invention.

For purposes of the invention, the amount or dose of the siNA compositions of the present invention that is administered should be sufficient to effectively target the cell, or population of cells in vivo, such that the modulation of the expression of the target gene of interest can be detected, in the subject over a reasonable time frame. The dose will be determined by the efficacy of the particular formulation and the location of the target population of cells in the subject, as well as the body weight of the subject to be treated.

The dose of the siNA compositions of the present invention also will be determined by the existence, nature and extent of any adverse side effects that might accompany the administration of a particular nanoparticle. Typically, an attending physician will decide the dosage of the composition with which to treat each individual subject, taking into consideration a variety of factors, such as age, body weight, general health, diet, sex, compound to be administered, route of administration, and the severity of the condition being treated. By way of example, and not intending to limit the invention, the dose of the compositions of the present invention can be about 0.001 to about 1000 mg/kg body weight of the subject being treated, from about 0.01 to about 100 mg/kg body weight, from about 0.1 mg/kg to about 10 mg/kg, and from about 0.5 mg to about 5 mg/kg body weight. In another embodiment, the dose of the compositions of the present invention can be at a concentration from about 1 nM to about 10,000 nM, preferably from about 10 nM to about 5,000 nM, more preferably from about 100 nM to about 500 nM.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer in a mammal. Furthermore, the treatment or prevention provided by the inventive method can include treatment or prevention of one or more conditions or symptoms of the disease, e.g., cancer, being treated or prevented. Also, for purposes herein, "prevention" can encompass delaying the onset of the disease, or a symptom or condition thereof.

In accordance with an embodiment, the siNA compositions of the present invention can be designed to down regulate or inhibit target gene expression through RNAi targeting of a variety of RNA molecules. In one embodiment, the compositions of the invention comprising siRNA molecules are used to target various RNAs corresponding to a target gene. Non-limiting examples of such RNAs include messenger RNA (mRNA), alternate RNA splice variants of target gene(s), post-transcriptionally modified RNA of target gene(s), pre-mRNA of target gene(s), and/or RNA templates. If alternate splicing produces a family of transcripts that are distinguished by usage of appropriate exons, the instant invention can be used to inhibit gene expression through the appropriate exons to specifically inhibit or to distinguish among the functions of gene family members. For example, a protein that contains an alternatively spliced transmembrane domain can be expressed in both membrane bound and secreted forms. Use of the siNA compositions of the present invention to target the exon containing the transmembrane domain can be used to determine the functional consequences of pharmaceutical targeting of membrane bound as opposed to the secreted form of the protein. Non-limiting examples of applications of the invention relating to targeting these RNA molecules include therapeutic pharmaceutical applications, pharmaceutical discovery applications, molecular diagnostic and gene function applications, and gene mapping.

The invention further provides a host cell comprising any of the compositions described herein. As used herein, the term "host cell" refers to any type of cell that can contain the inventive siNA compositions. The host cell can be a eukaryotic cell, e.g., plant, animal, fungi, or algae. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, HeLa cells (human epithelial cervical cancer cell line), D407 cells (human retinal pigmented epithelial cell line), Chinese hamster ovarian cells, monkey VERO cells, COS cells, HEK293 cells, MCF-7 cells and the like. For purposes of modulating the expression of a target gene of interest in a cell, the host cell is preferably a mammalian cell. Most preferably, the host cell is a human cell. Examples of suitable human host cells can include, but are not limited to, cells of the major organs of the body, including, for example, cells of the lung, including hepatocytes and hepatic stellate cells, cells of the breast, cells of the prostate, cells of the cornea, including corneal epithelial cells, cells of the lung, including lung epithelial cells, and cells of the brain, such as neurons. While the host cell can be of any cell type, can originate from any type of tissue, and can be of any developmental stage, the host cell preferably is a cancer cell.

The population of cells can be a heterogeneous population comprising the host cell comprising any of the compositions described, in addition to at least one other cell, e.g., a host cell (e.g., a epithelial cell), which does not comprise any of the compositions, or a cell other than a epithelial cell, e.g., a macrophage, a neutrophil, an erythrocyte, a hepatocyte, a hepatic stellate cell, an endothelial cell, an epithelial cell, a muscle cell, a brain cell, etc. Alternatively, the population of cells can be a substantially homogeneous population, in which the population comprises mainly of host cells (e.g., consisting essentially of) comprising the compositions.

In accordance with an embodiment of the present invention, the medicament for treating a disease in a subject can encompass many different formulations known in the pharmaceutical arts, including, for example, intravenous and sustained release formulations. With respect to the inventive methods, the disease can include cancer. Preferably, the cancer is breast cancer.

In another embodiment, the term "administering" means that at least one or more siNA compositions of the present invention are introduced into a subject, preferably a subject receiving treatment for a disease, and the at least one or more siNA compositions are allowed to come in contact with the one or more disease related cells or population of cells having the target gene of interest in vivo.

As used herein, the term "treat," as well as words stemming therefrom, includes diagnostic and preventative as well as disorder remitative treatment.

As used herein, the term "subject" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

The siNA compositions of the present invention can be used in a variety of diagnostic applications, such as in the identification of molecular targets (e.g., RNA) in a variety of applications, for example, in clinical, industrial, environmental, agricultural and/or research settings. Such diagnostic use of siRNA containing nanoparticles involves utilizing reconstituted RNAi systems, for example, using cellular lysates or partially purified cellular lysates. siRNA in nanoparticles of the present invention can be used as diagnostic tools to examine genetic drift and mutations within diseased cells or to detect the presence of endogenous or exogenous, for example viral, RNA in a cell. The close relationship between siRNA activity and the structure of the target RNA allows the detection of mutations in any region of the molecule, which alters the base-pairing and three-dimensional structure of the target RNA. By using multiple siRNA molecules in the nanoparticles of the present invention, one can map nucleotide changes, which are important to RNA structure and function in vitro, as well as in cells and tissues. Cleavage of target RNAs with siRNA molecules can be used to inhibit gene expression and define the role of specified gene products in the progression of disease or infection, or other clinical condition. In this manner, other genetic targets can be defined as important mediators of the disease.

These experiments will lead to better treatment of the disease progression by affording the possibility of combination therapies (e.g., multiple siRNA molecule containing nanoparticles targeted to different genes, siRNA molecule containing nanoparticles coupled with known small molecule inhibitors, or intermittent treatment with combinations siRNA molecules and/or other chemical or biological molecules). Other in vitro uses of siRNA containing nanoparticles of the present invention are well known in the art, and include detection of the presence of mRNAs associated with a disease, infection, or related condition. Such RNA is detected by determining the presence of a cleavage product after treatment with a siRNA using standard methodologies, for example, fluorescence resonance emission transfer (FRET).

EXAMPLES

Cell lines, cell culture and reagents. The pcDNA3 vectors or pcDNA3-Flag-HOXB7 vectors were stably transfected into MCF 10A cells, or MCF-7 cells, by use of Effectene (Qiagen, Valencia, Calif.). MCF-7-LTED, the estrogen hypersensitive MCF-7 subline was generated from MCF-7 cells by long-term culture under estrogen-deprived conditions and are called long-term estradiol-deprived (LTED) cells (*Endocrinology* 139(10):4164-4174), was a kind gift of Dr. Richard Santen. LTED cells are refractory to tamoxifen but sensitive to fulvestrant (11). MCF-7-TAMLT Long-term tamoxifen-stimulated tumor (MCF-7 TAMLT), kindly provided by V. Craig Jordan, was developed by re-transplanting growing estradiol-dependent MCF-7 tumors into new athymic mice and treating the mice with tamoxifen for more than 5 years. Fulvestrant and Iressa (gefitinib) were provided by Astrazeneca (Cheshire, U.K.).

Luciferase Reporter Assay. Transient transfection was performed with the respective promoter-luciferase constructs. Results were normalized to the level of β-galactosidase activity in the samples. The EGFR promoter reporter plasmids were a kind gift of Dr. Alfred C. Johnson (Bethesda, Md.). ERE-tk-LUC was a generous gift from Dr. Elaine Alarid (Madison, Wis.).

Small Interfering Nucleic Acid (siNA) Preparation and Transfection. The siRNA sequences used for targeting human HOXB7 were: 5'-ATA TCC AGC CTC AAG TTC G-3' (SEQ ID NO: 1) and 5'-ACT TCT TG TGC GTT TGC TT-3' (SEQ ID NO: 2). The two HOXB7 siRNA expression plasmids were mixed 1:1 for transfection by use of Effectene (Qiagen).

Xenograft Analysis. About 3×10$^6$ cells of MCF-7-vec or MCF-7-B7 were suspended in 100 µl PBS/Matrigel (1:1) and injected s.c into the female 3- to 4-week-old BALB/c nu/nu athymic mice (Harlan, Sprague Dawley, Madison, Wis.), which simultaneously received a 60-day slow release pellet containing 0.72 mg of 17β-estradiol and/or 5 mg tamoxifen (Innovative Research of America, Southfield, Mich.). Animals were observed once a week. At necropsy, primary tumors, liver, lung and spleen were evaluated for the presence of macroscopic tumors. Tissue samples of the primary tumor and organs were fixed in 4% paraformaldehyde and stained with H&E to assess histomorphology.

Chromatin Immunoprecipitation (ChIP) Assay. ChIP assays were performed essentially as described in (36), the IP using anti-Flag M2 antibody or control IgG, and amplification of the DNA in the complex using the following primers for EGFR promoter region (sense 5'-CAA GGC CAG CCT CTG AT-3' (SEQ ID NO: 3), anti-sense 5'-CCC CTT TCC CTT CTT TTG TT-3' (SEQ ID NO: 4). PCR products were analyzed by agarose gel electrophoresis.

FISH analysis. HOXB7 copy number levels were determined by FISH on the TMA as described (37). HOXB7 specific BAC clone (RP11-361K8) was labeled with SpectrumOrange (Vysis, Downers Grove, Ill.) and SpectrumGreen-labeled chromosome 17 centromere probe (Vysis) was used as a reference. The nuclei were counterstained with DAPI. The entire tissue core was screened, with a minimum of 50 intact nuclei scored for each specimen. A total of 280 samples were successfully analyzed. Tumor samples containing a 3-fold or higher increase in the number of HOXB7 signals as compared with centromere signals were considered to be amplified.

Real-time PCR of HOXB7 expression. HOXB7 gene expression was quantitated by Taqman real-time quantitative PCR in triplicate in 96-well plate using an ABI 7900HT (Applied Biosystems) using cDNA derived from our previously published cohort of tumor samples (*Cancer research* 62(3):827-834). The sequences of the HOXB7 PCR primer pairs and fluorogenic MGB probe (5' to 3'), respectively, are: AAA ACC TAC CAC TCG CGT GTT C (SEQ ID NO: 5), GGA CGG GAA GCA AGA AGC A (SEQ ID NO: 6), and VIC-CAA GCG CCT GGC TG (SEQ ID NO: 7).

Statistical Analysis. HOXB7 expression levels determined by RT-PCR were dichotomized into low and high groups using the median as cutoff. Kaplan-Meier analysis and log-rank tests were performed to assess the association of HOXB7 groups with distant metastasis-free survival. All statistical tests were two-sided, and differences were considered statistically significant at P<0.05. All analyses were performed using SAS (version 9.1, Cary, N.C.) and R (version 2.4.1).

Example 1

Figure 1B:
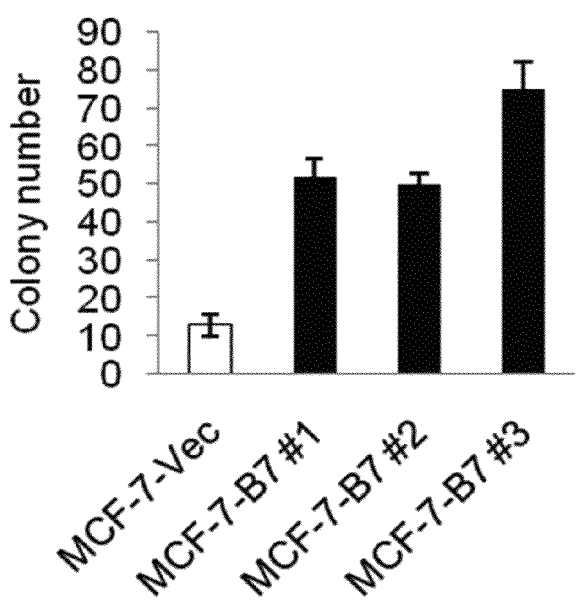
Figure 1C:
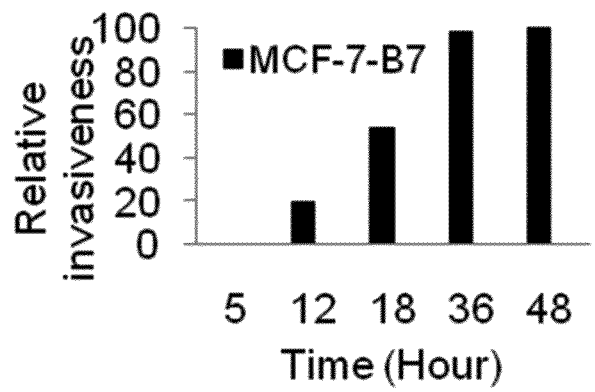
Figure 1D:
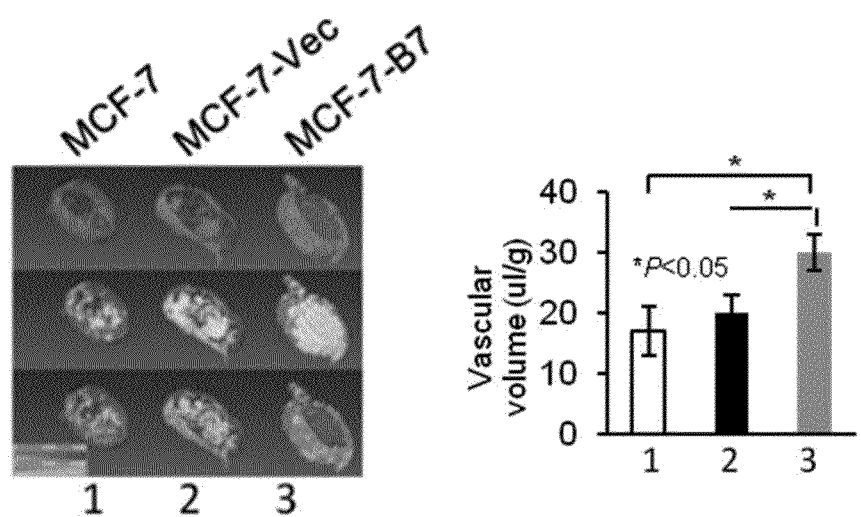
Figure 1E:
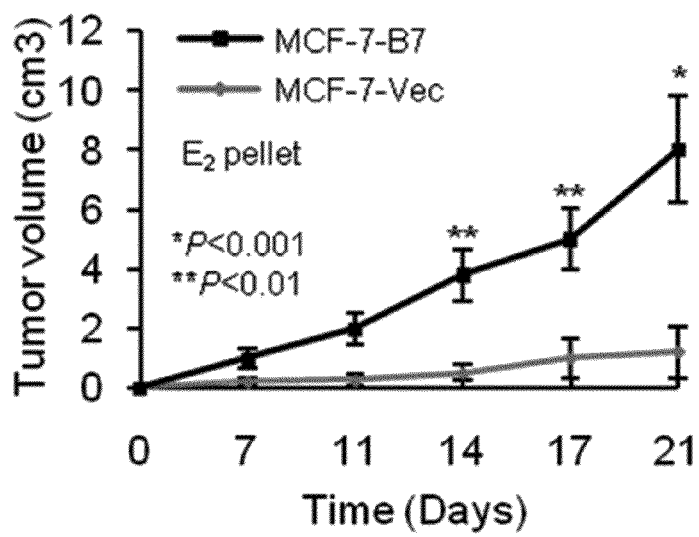

HOXB7 expression promotes breast tumorigenesis. Breast cancer cells, MCF-7, are estrogen-dependent for growth in vitro and in vivo and are susceptible to the cytostatic/cytotoxic effects of TAM. Stable expression of a HOXB7 expression vector in MCF-7 cells (3 clones; MCF-7-B7 #1, #2 and #3) enabled the cells to proliferate much faster than the vector control cells (MCF-7-Vec) in monolayer cultures and significantly enhanced colony formation (FIGS. 1A, 1B). Magnetic resonance imaging (MRI) analysis of invasion of cells through extra-cellular matrix revealed that MCF-7-B7 cells but not MCF-7 cells were highly invasive in vitro and were significantly hypervascular in vivo (FIG. 1C, 1D) without any significant change in permeability. Consistent with these observations, when transplanted to the athymic nude mice s.c. in presence of exogenous estrogen supplementation, MCF-7-B7 cells formed faster growing, and larger tumors compared to the MCF-7-Vec cells (FIG. 1E). Tumors formed by MCF-7-Vec cells were grossly well-defined and loosely attached to surrounding tissue while MCF-7-B7 cells grew as highly invasive tumors firmly attached to surrounding tissues, infiltrating the underlying skeletal muscle and fat tissue (data not shown). Thus, HOXB7 overexpression promoted invasive and aggressive growth of the MCF-7-B7 cells.

Figure 1F:
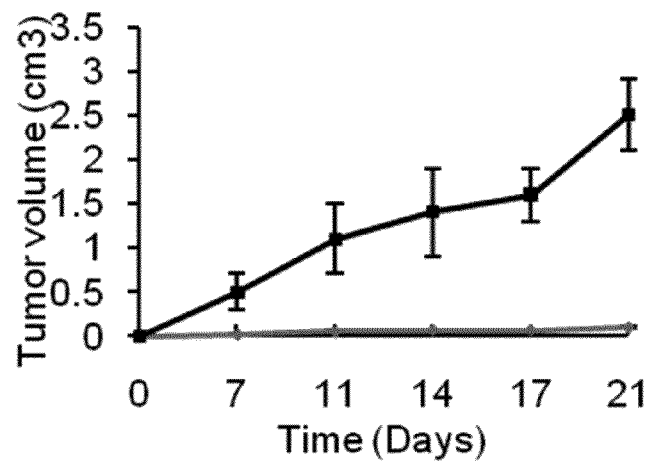

One of the hallmarks of cancer is self-sufficiency in growth signals. A reduced need for estrogen by ER+ cells is often linked to their resistance to TAM treatment. HOXB7 overexpression in MCF-7 cells resulted in a much reduced dependence on nutrients. MCF10A-B7 cells proliferated in low growth factor supplemented medium and MCF-7-B7 cells grew in estrogen-deprived medium, while vector-transfected cells barely survived (data not shown). In vivo, even in the absence of exogenous estrogen supplementation, MCF-7-B7 cells formed rapidly growing tumors in athymic nude mice (FIG. 1F), while MCF-7-vec cells did not form palpable tumors. Thus, HOXB7 overexpression enabled MCF-7 cells to largely circumvent the need for exogenous estrogen for growth.

Example 2

Figure 2A:
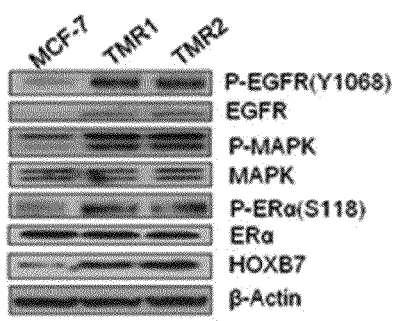
FIG. 2 shows that HOXB7 promotes acquired TAM resistance. (2A) Immunoblot analysis of Phospho-EGFR (Y1068), EGFR, Phospho-MAPK, MAPK, Phospho-ERα (S118), ERα, and HOXB7 expression in MCF-7 cells treated long-term with either vehicle or 0.1 μM TAM (TMR1) or 1 μM TAM (TMR2). (2B) Immunoblot analysis of EGFR, Phospho-MAPK, MAPK and HOXB7 expression in MCF-7-TMR cells and BT474 transfected with either scrambled sequence siRNA or HOXB7-specific siRNA. (2C) Soft agar colony formation in BT474 cells and MCF-7-TMR cells transfected with either scrambled sequence siRNA or HOXB7-specific siRNA treated with Vehicle or 1 μM TAM. (2D) Soft agar colony formation by BT474 cells and MCF-7-TMR cells treated with 1 μM gefitinib and 1 μM TAM.

HOXB7 in the acquisition of anti-estrogen resistance. Because of the observation of a striking similarity in phenotype between prolonged endocrine therapy primed TAM-resistant models and our HOXB7 overexpressing cells, the hypothesis that HOXB7 is a mediator of anti-estrogen resistance was investigated. MCF-7 cell lines were derived, and exposed to either vehicle or TAM (0.1 μM or 1 μM) for over 12 months (designated MCF-7-TMR1 or MCF-7-TMR2 respectively). MCF-7-TMR1 cells exhibited significant resistance to TAM treatment as determined by colony formation assay (data not shown). Long-term TAM treatment caused elevated expression of EGFR and activated MAPK and ERα, but no significant change of total ERα. It was also found that HOXB7 was upregulated in MCF-7-TMR cells (FIG. 2A). In addition, over time (0, 2, 4, 6 months) MCF-7 cells treated with 0.1 μM TAM showed progressively increasing levels of HOXB7 expression, accompanied by concomitant increase in expression of EGFR (data not shown).

Example 3

Figure 2B:
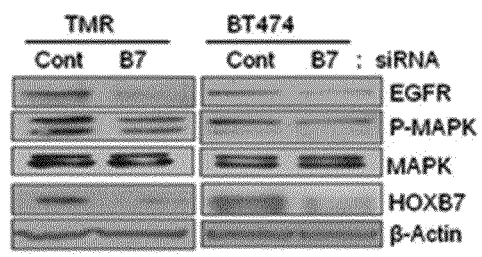
Figure 2C:
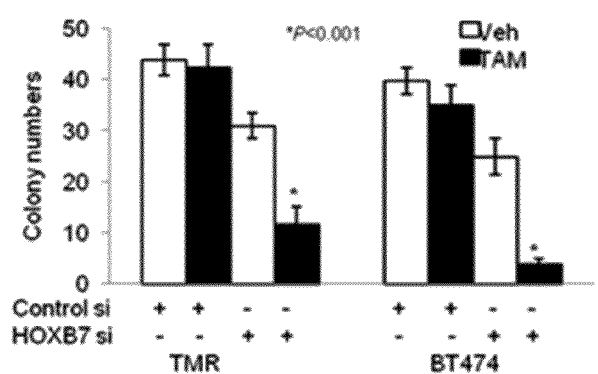
Figure 2D:
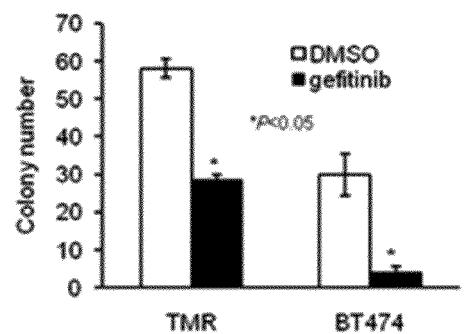

In order to investigate whether HOXB7 overexpression is key event in TAM resistance through EGFR expression, HOXB7 expression was depleted with HOXB7 siRNA in MCF-7-TMR cells. Remarkably, abrogation of HOXB7 expression by siRNA reversed each of the observed molecular events in the MCF-7-TMR cells and direct evidence of a role for HOXB7 was sought in an unmanipulated, TAM-resistant breast cancer cell line, BT474 (FIG. 2B). Here, reduction of endogenous HOXB7 expression using HOXB7-siRNAs was sufficient to reduce the expression levels of EGFR and P-MAPK with regained sensitivity to TAM (FIG. 2C). An in vitro, long-term estrogen deprivation model, MCF-7-LTED was tested. Expression of HOXB7 and EGFR was examined in cell lysates in an in vitro, long-term estrogen deprivation model, MCF-7-LTED, and in an in vivo, long term TAM-treated xenograft model, MCF-7-TAMLT, along with our MCF-7-TMR model. In line with previous observations, HOXB7 and EGFR expression was elevated in both models (data not shown). Abrogation of EGFR dependent pathway is critical for HOXB7-siRNAs elicited effect, since an EGFR specific inhibitor, gefitinib, dramatically converted TAM to a potent antagonist in MCF-7-TMR and BT474 cells (FIG. 2D). Thus, indicating that HOXB7 is an important drug target, whose functional antagonism impinges on EGFR pathway important to TAM resistance.

Example 4

Figure 3A:
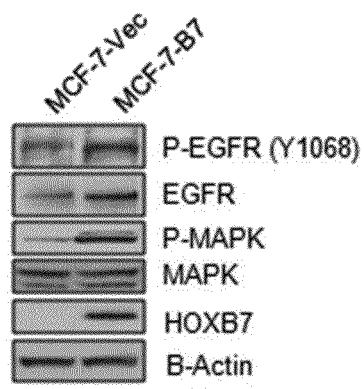
FIG. 3 depicts evidence that HOXB7 promotes TAM resistance. (3A) Immunoblot analysis of Phospho-EGFR, EGFR, P-MAPK, MAPK and HOXB7 expression levels in MCF-7-Vec and MCF-7-HOXB7 cells. (3B) Tumor growth curve of MCF-7-HOXB7 cells implanted s.c. in athymic Swiss female mice and treated with either vehicle or TAM (83.3 μg/day), in the absence of an exogenous estrogen supplement. (3C) Soft agar colony formation by MCF-7-vec and MCF-7-B7 cells treated with either vehicle, estrogen (10 nM) or TAM (1 μM) and combination with 1 μM gefitinib as indicated. (3D) Semi quantitative RT-PCR analysis of mRNA expression levels of TGFα, HB-EGF and Amphiregulin in HOXB7 expressing MCF-7 cells and their vector controls (left); Amphiregulin or TGFα mRNA expression in MCF-7-vec and MCF-7-B7 cells treated with either scrambled sequence siRNA or ERα-specific siRNA (right) (3E) Diagram representing the HOXB7 binding sites in EGFR promoter region. MCF-7 cells were transfected with pcDNA3-Flag-HOXB7 and Vector plasmid, ChIP was performed by IP with either anti-Flag M2 antibody or control IgG. (3F) Luciferase activity of deletion/truncation constructs of the EGFR promoter, with (solid box) and without (slashed box) transfected HOXB7 plasmid, to map minimal region necessary for activation by HOXB7.

HOXB7 promotes tamoxifen resistance. Since it was found that expression of HER1/EGFR was upregulated in HOXB7-expressing breast cancer cells, the mechanism by which HOXB7 might regulate HER1/EGFR was investigated. Stable overexpression of HOXB7 in MCF-7 cells resulted in increased expression of EGFR, elevated tyrosine phosphorylation at the kinase domain (Y1068) of EGFR and the major downstream effector, p44/42 MAPK, was activated as well (FIG. 3A).

Figure 3B:
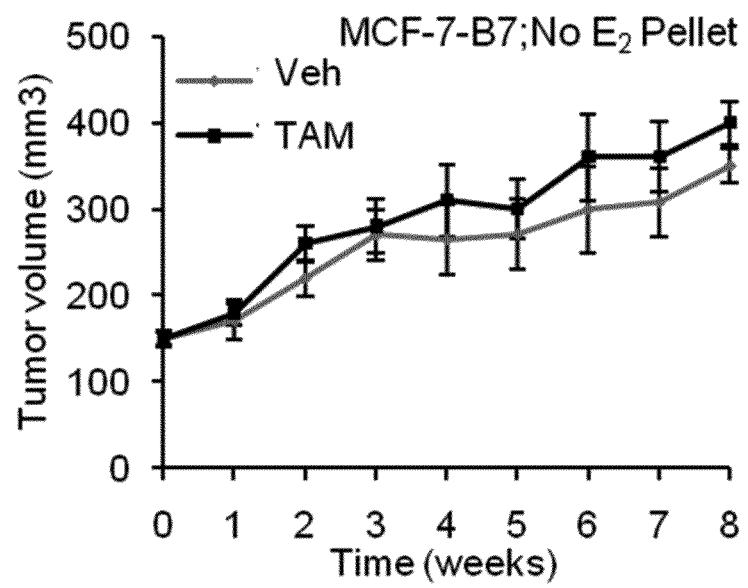

Next, the biological properties of MCF-7-B7 cells were tested. In culture, TAM treatment of MCF-7-Vec cells led to increased apoptosis and decreased cell viability while MCF-7-B7 cells were minimally sensitive. The TAM-resistant property of MCF-7-B7 cells was also verified by the estrogen-stimulated ERE-luc reporter activity in these cells. Further, MCF-7-B7 cells formed colonies in soft agar in the presence of tamoxifen at frequencies similar to vehicle treated cells. Notably, unlike vector control cells, MCF-7-B7 xenografts in immunodeficient mice failed to respond to the inhibitory effects of TAM (FIG. 3B). Thus, by all these growth criteria, the behavior of the MCF-7-B7 cells was very similar to MCF-7-TMR cells described above.

Figure 3C:
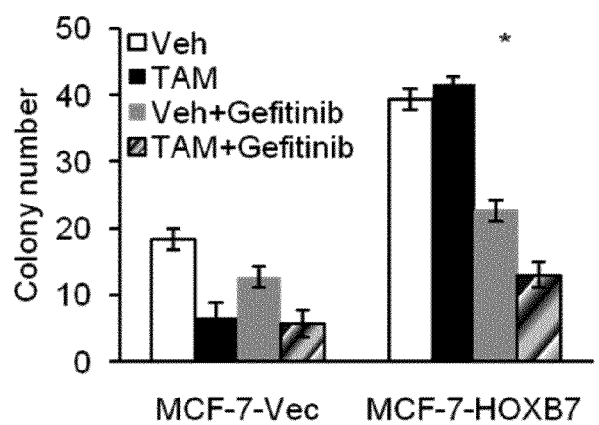

Abrogation of EGFR activity in MCF-7-B7 cells by the EGFR-specific inhibitor, gefitinib, significantly re-sensitized them to TAM treatment (FIG. 3C). To determine if the HOXB7/EGFR crosstalk is rapid and direct, estrogen deprived MCF-7-B7 cells were treated with 1 μM TAM for 0-30 minutes; this led to elevated phosphorylation of EGFR, activation of p44 MAPK, and ER phosphorylation at Serine 118 (data not shown). These observations indicate that under the treatment conditions, nongenomic ERα action occurred to activate EGFR signaling. This effect was sustained for longer periods of time; MCF-7-B7 cells grown in estrogen deprived conditions exposed to TAM for 24 hours also led to the expression of significantly higher levels of active forms of EGFR, increased p44/42 MAPK activity and ERα phosphorylation, in contrast to control MCF-7-Vec cells.

Elevated activation of EGFR as a result of HOXB7 overexpression prompted an examination of possible over-production of known EGFR ligands (i.e. TGFα, ARG and HB-EGF). Indeed, increased mRNA expression of the three EGFR ligands was observed in MCF-7-B7 cells (FIG. 3D), as well as in MCF-7-TMR and MCF10A-B7 cells (data not shown). Consistent with increased mRNA levels, a significant increase of TGFα and HB-EGF expression was detected at the protein level in MCF-10A-B7 cells. The elevated expression of TGFα and HB-EGF was significantly abrogated by the pharmacological inhibition of EGFR activity using the EGFR-kinase inhibitor, AG1478 and gefitinib. This indicates the possible existence of a positive feedback mechanism for the synergistic activation of EGFR pathways as a result of HOXB7 expression in MCF10A cells. Increased expression of TGFα and HB-EGF was also found upon overexpression of exogenous HOXB7- in ER-negative breast cancer cell lines, SKBR3, MDA-MB-231 and MDA-MB-435. Conversely, the expression level of these ligands was decreased by depletion of HOXB7 by siRNA. However, it is likely that in MCF-7-B7 cells an alternative pathway, such as overexpressed HOXB7 acting through ERα, regulates the overproduction of autocrine/paracrine EGFR ligands.

Figure 3D:
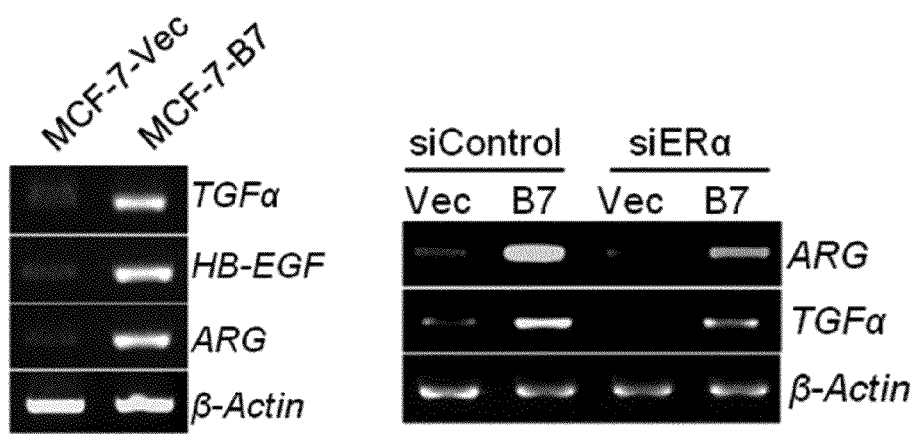

To further examine possible cross-talk between EGFR and ER-signaling as a result of HOXB7 overexpression, the ER-downregulator, fulvestrant (ICI-182780, Faslodex) was utilized. Fulvestrant treatment modestly reduced increases in EGFR and p44/42 MAPK activity upon HOXB7 overexpression. Consistent with reduced EGFR activity, a significant reduction in levels of the autocrine/paracrine EGFR ligands (ARG and TGFα) were observed in fulvestrant-treated MCF-7-B7 cells (data not shown). A positive role for ERα in these effects of HOXB7 was indicated by partial reduction in levels of ARG and TGFα upon ERα-specific siRNA transfection of MCF-7-B7 cells (FIG. 3D). Thus, ER-dependent pathways are responsible for elevated levels of the autocrine/paracrine EGFR ligands in MCF-7-B7 cells, which results in elevated EGFR signaling.

Example 5

Figure 3E:
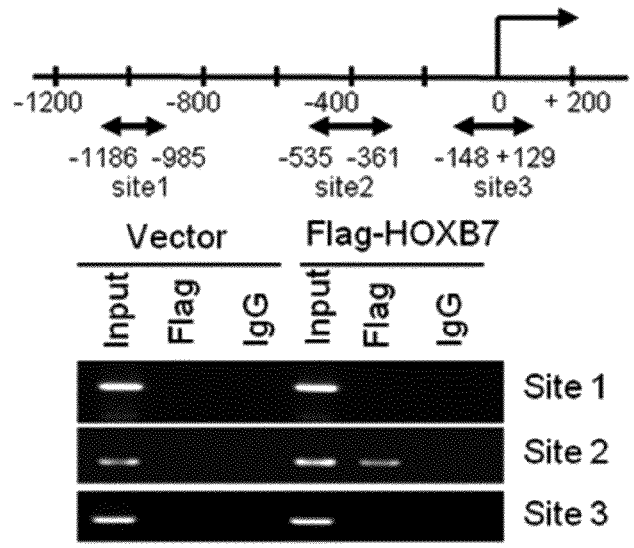
Figure 3F:
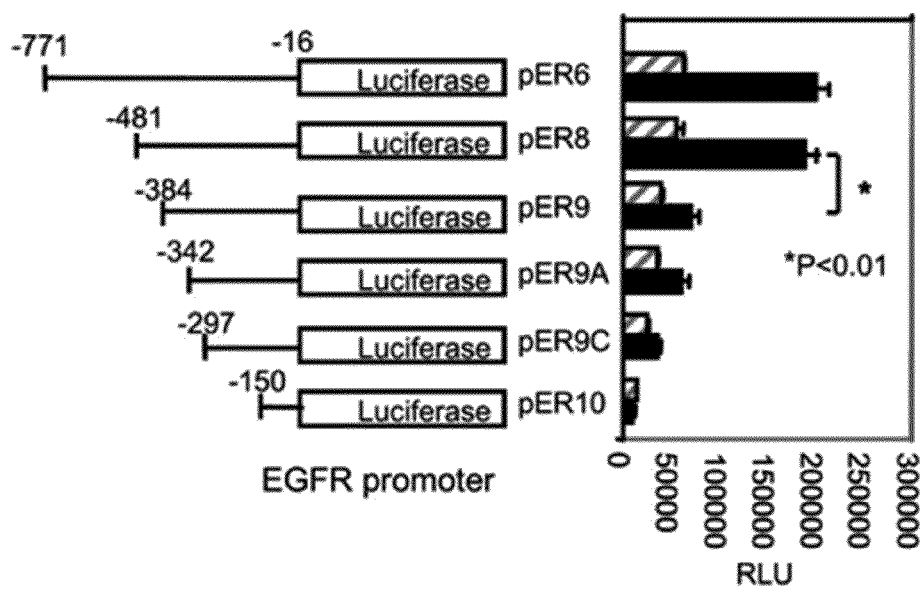

To examine if the interaction between HOXB7 and EGFR is direct, ChIP assays were performed. A single putative HOXB7-binding site was identified in the 800 bp EGFR promoter (FIG. 3E). To provide supportive evidence, luciferase reporter constructs containing serial deletions of the EGFR promoter (Cancer research, 62(21):6240-6245) were co-transfected into MCF-7 and MCF10A cells along with the HOXB7 expression plasmids. As shown in FIG. 3F, both pER6-luc containing nucleotides −771 to −16, and pER8-luc containing nucleotides −481 to −16 were activated 2.5- to 3-fold by HOXB7, whereas pER9-luc containing nucleotides −342 to −16, −297 to −16, or −150 to −16 were activated at much lower levels in MCF-7 cells (FIG. 3F). These results were consistent with the ChIP assay data localizing sequences necessary for response of EGFR to HOXB7.

An upregulation of EGFR in HOXB7 overexpressing MCF10A and HBL-100 cells was also found (data not shown). EGFR and p44/42 MAPK activities were also reduced by HOXB7 siRNA expression in ER-negative MDA-MB-435 and MDA-MB-468 cells. Moreover, transfection of HOXB7 siRNA into MCF-7-HOXB7 cells was also able to re-sensitize them to TAM treatment (data not shown). These results indicate that HOXB7 should be an attractive anti-cancer target in both ER+ and ER− tumors. Thus, these data strongly support the conclusion that HOXB7 is an important mediator of the cross-talk between EGFR and ERα signaling which is critical for maintaining resistance to TAM in MCF-7 cells.

Example 6

The underlying mechanism of HOXB7 overexpression in TAM-resistant breast cancer cells was investigated. An investigation into whether HOXB7 overexpression in breast tumors could be traced to gene amplification was undertaken by performing FISH on tissue microarrays of primary breast tumors. However, only 2 of 172 Swedish cases, and 1 of 108 Finnish cases showed amplification of HOXB7 (data not shown). Based on this data, it was concluded that gene amplification is not a major mechanism underlying elevated expression of HOXB7 in breast cancer, including tamoxifen-resistant cancer.

Figure 4A:
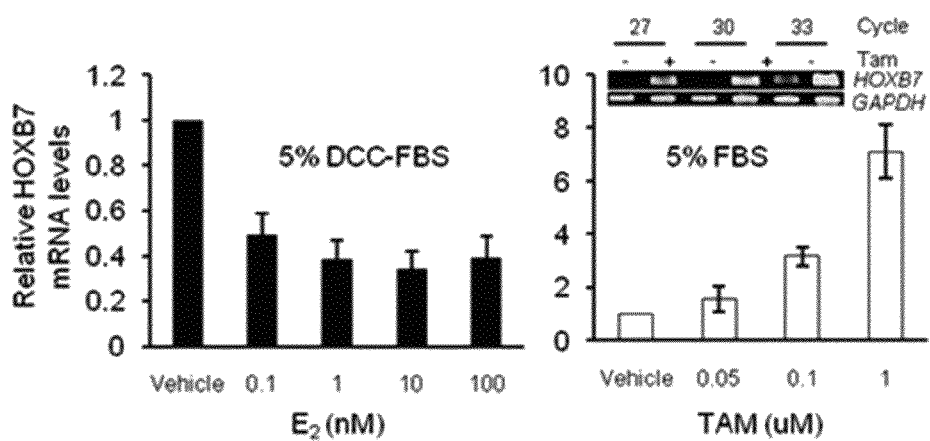
FIG. 4 shows how the ERα regulates HOXB7 expression. (4A) Real time quantitative PCR analysis of HOXB7 mRNA levels in MCF-7 cells. Cells were incubated in estrogen deprived condition for 72 hours [DMEM phenol red-free medium containing 5% Dextran charcoal stripped serum (DCC-FBS)]; the cells were then treated with 0.1-100 nM estrogen ($E_2$); Cells were treated with 0.05 to 1 μM of TAM in DMEM plus 5% FBS; Inset: Semi-quantitative RT-PCR analysis of HOXB7 mRNA following 1 uM TAM treatment for 24 hour. (4B) Real time quantitative PCR analysis of HOXB7. mRNA levels in MDA-MB-231 and MDA-MB-453 cells were transiently transfected with ERα expression plasmid and vector control for 48 hours. ERIN, a ERα overexpressed cell line, was used with MCF10A as a control. (4C) Immunoblot analysis of HOXB7 and ERα expression levels in transient transfectants of MDA-MB-231-ERα.
Figure 4B:
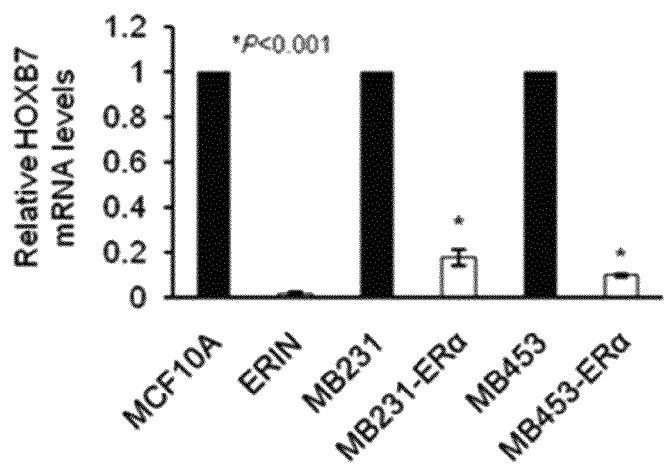
Figure 4C:
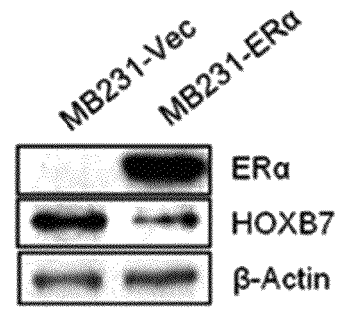

HOXB7 mRNA levels increased upon treatment of MCF-7 and T47D cells with tamoxifen in medium containing 10% FBS (i.e. abundance of estrogen) (FIG. 4A). In addition, HOXB7 mRNA levels increased in estrogen-deprived growth conditions (5% charcoal stripped serum). Interestingly, HOXB7 expression was significantly reduced with estradiol stimulation under the same conditions (FIG. 4A). The downregulation of HOXB7 expression by estradiol is abrogated by tamoxifen. To further test this concept, ERα were overexpressed in ER-negative cell lines such as MDA-MB-231, MDA-MB-453 and MCF10A. It was observed that HOXB7 expression was dramatically decreased in the ERα overexpressing cells (FIG. 4B, 4C). These findings support the hypothesis that HOXB7 expression is regulated by estrogen, and this action is dependent on the presence of a functional ERα.

Example 7

Figure 5A:
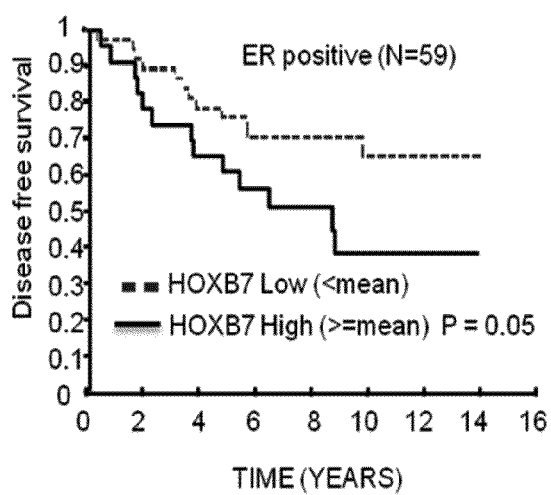
FIG. 5 depicts Kaplan-Meier plots of disease-free survival analysis of estrogen receptor-positive node negative patients who (5A) received TAM monotherapy (N=59) and (5B) no adjuvant therapy after surgery (N=209), and were stratified by HOXB7 expression level. (5C) Pearson correlation between HOXB7 and EGFR mRNA level in breast cancer patient samples (N=57). (5D) Pearson correlation between HOXB7 and EGFR protein levels by IHC in breast cancer patient sample TMA (N=127).
Figure 5B:
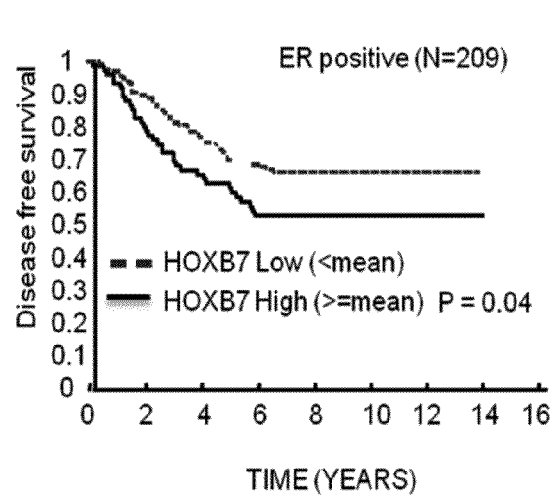
Figure 5C:
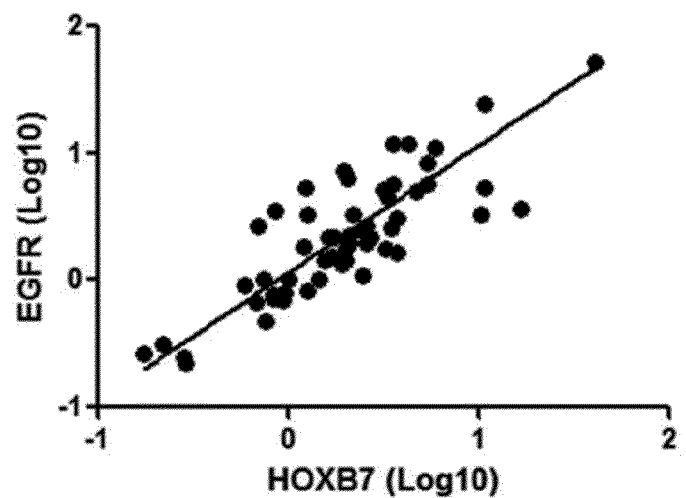
Figure 5D:
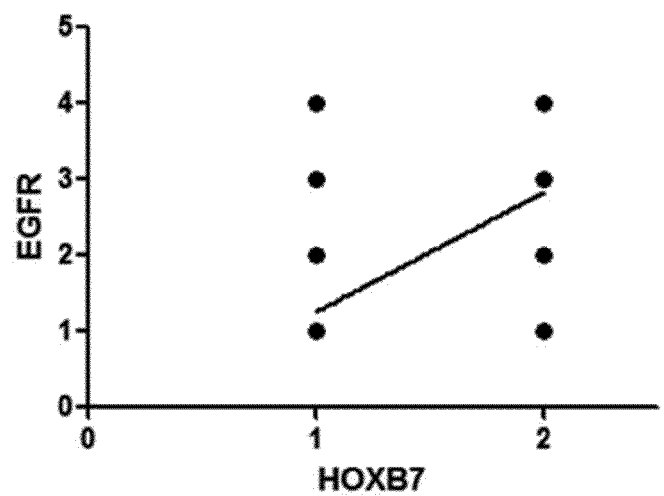

Based on the ability of overexpressed HOXB7 to lead to TAM resistance, it was investigated whether HOXB7 overexpression in primary tumors may predict subsequent TAM resistance. HOXB7 mRNA levels of hormone receptor-positive primary breast cancers were examined in two different small sets of patients (n=59 and n=72) treated with adjuvant TAM-monotherapy (Cancer Cell, 5(6):607-616) and 209 patients with no adjuvant therapy after surgery by real-time PCR. In these discovery sets of tissues, the association between higher expression level of HOXB7 and poorer relapse-free survival was statistically significant (FIGS. 5A and 5B), indicating that elevated expression levels of HOXB7 was associated with the development of tamoxifen resistance in breast cancer patients. In addition, to investigate whether there was a correlation between HOXB7 and EGFR expression in clinical cohorts. HOXB7 and EGFR mRNA levels were examined by qRT-PCR in 57 breast cancer patient samples and 48 breast cancer cell lines. In addition, 127 breast cancer patient samples were investigated by IHC using a breast cancer tissue microarray. A correlation between HOXB7 and EGFR was observed both at the mRNA level ($r=0.8772, 0.8290$) and IHC detection ($r=0.6341$) with statistical significance ($P<0.0001$) (FIGS. 5C and 5D). Collectively, the present invention provides that elevated HOXB7 expression under various scenarios serves as a unifying molecular hub directing the development of anti-estrogen resistance.

Example 8

Figure 6A:
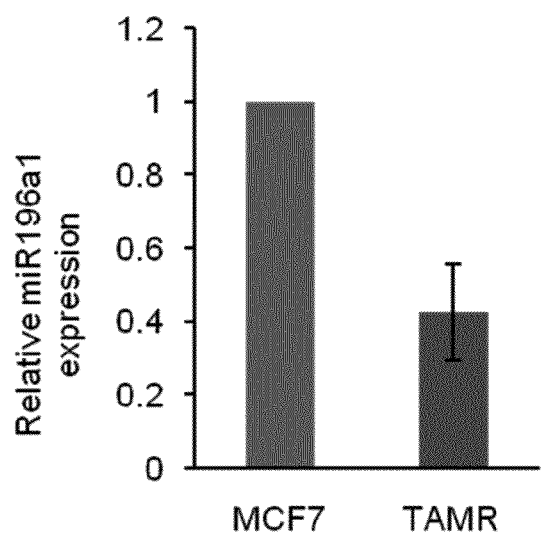
FIG. 6 shows that HOXB7 is a target of miRNA-196a. It was found that the level of miR-196a expression was downregulated in TAMR compared to the parental cells (6A). In addition, overexpression of miR-196a blocked HOXB7 expression as well as HER2 expression in both TAMR cells and MDA-MB-453 cells, a HER2 positive breast cancer cell line (6B). Using an established HOXB7-3'UTR Luciferase construct, we confirmed the inhibitory effect of miR-196a to HOXB7 transcription (6C). We also found that enforced miR196a expression enhanced re-sensitized TAMR cells with TAM treatment (6D). Immunoblotting analysis comparing vector control and miR-196a-TMR cells showed decrease of HER expression as well as Cyclin D1 and MYC as ER target genes due to inhibition of HOXB7 expression (6E).
Figure 6B:
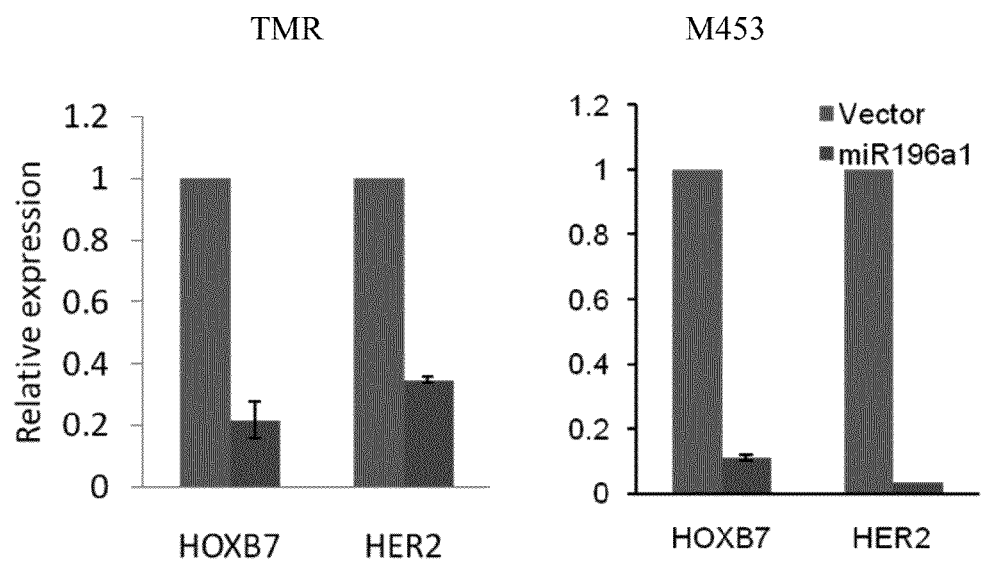

HOXB7 as a target of miRNA-196a. The next investigation was to determine by what mechanism was HOXB7 expression upregulated in TAMR cells. It was hypothesized that in TAMR cells the upregulation of HOXB7 could be caused by reduced the level of miR-196a. Consistent with our hypothesis, it was found that the level of miR-196a expression was downregulated in TAMR compared to the parental cells (FIG. 6A). In addition, overexpression of miR-196a blocked HOXB7 expression as well as HER2 expression in both TAMR cell and MDA-MB-453 cells, a HER2 positive breast cancer cell line (FIG. 6B).

Figure 6C:
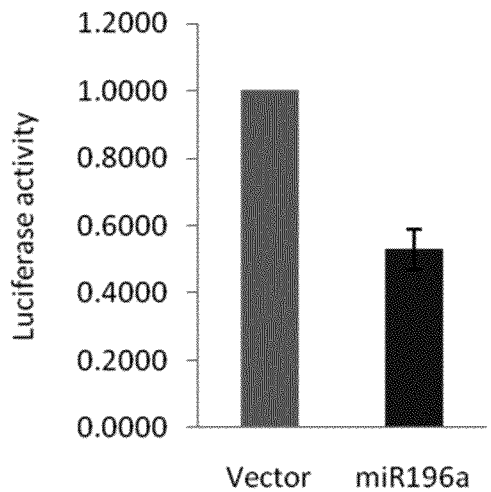
Figure 6D:
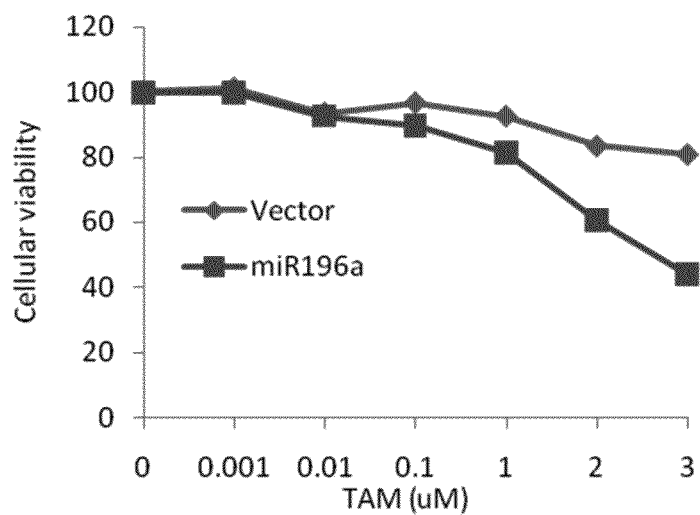
Figure 6E:
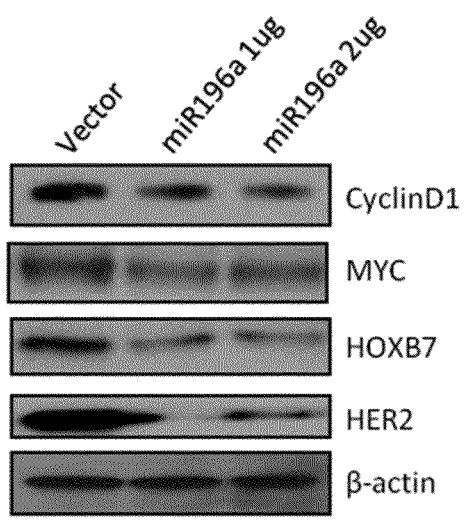

Using established HOXB7-3'UTR Luciferase construct, we confirmed the inhibitory effect of miR-196a to HOXB7 transcription (FIG. 6C). We also found that enforced miR196a expression enhanced re-sensitized TAMR cells with TAM treatment (FIG. 6D). Immunoblotting analysis comparing vector control and miR-196a-TMR cells showed decrease of HER expression as well as Cyclin D1 and MYC as ER target genes due to inhibition of HOXB7 expression (FIG. 6E). Our finding suggested that the lower miR-196a levels induced HOXB7 upregulation in TMR.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of predicting an increased risk of non-responsiveness to treatment with tamoxifen in a patient suffering from breast cancer comprising:
   a) obtaining a sample of mRNA from a tumor of the patient;
   b) performing quantitative real-time PCR on the sample of a) to measure the level of mRNA expression of the HOXB7 gene using the qRT-PCT primers and probes consisting of SEQ ID NOS: 5-7;
   c) providing a reference non-tamoxifen resistant tumor sample and performing quantitative real-time PCR on the non-tamoxifen resistant tumor sample to measure the level of mRNA expression of the HOXB7 gene using the qRT-PCT primers and probes consisting of SEQ ID NOS: 5-7;
   d) comparing the level of the level of mRNA expression of the HOXB7 gene in the tumor sample of the patient, to the level of the level of mRNA expression of the HOXB7 gene in the reference non-tamoxifen resistant tumor sample;
   e) identifying said patient as having an increased risk of non-responsiveness to treatment with tamoxifen in the tumor of the patient based on the level of expression of HOXB7 in the tumor, when the level of expression of HOXB7 is elevated when compared to a reference non-tamoxifen resistant tumor sample; and
   f) adjusting the chemotherapeutic and/or treatment regimen of the patient to address the increased risk of tamoxifen resistance.

2. A method predicting a clinical outcome after treatment with tamoxifen in a patient suffering from breast cancer comprising:
   a) obtaining a sample of mRNA from a tumor of the patient;
   b) performing quantitative real-time PCR on the sample of a) to measure the level of mRNA expression of the HOXB7 gene using the qRT-PCT primers and probes consisting of SEQ ID NOS: 5-7;
   c) providing a reference non-tamoxifen resistant tumor sample and performing quantitative real-time PCR on the non-tamoxifen resistant tumor sample to measure the level of mRNA expression of the HOXB7 gene using the qRT-PCT primers and probes consisting of SEQ ID NOS: 5-7;
   d) comparing the level of the level of mRNA expression of the HOXB7 gene in the tumor sample of the patient, to the level of the level of mRNA expression of the HOXB7 gene in the reference non-tamoxifen resistant tumor sample;
   e) predicting the outcome of treatment with tamoxifen in the patient based on the level of expression of HOXB7 in the tumor,
   wherein when the level of expression of HOXB7 is elevated when compared to a reference non-tamoxifen resistant tumor sample there is a prediction of a decrease in relapse-free survival outcome in the patient.

* * * * *